US006773882B2

(12) United States Patent
Hogan et al.

(10) Patent No.: US 6,773,882 B2
(45) Date of Patent: Aug. 10, 2004

(54) POLYNUCLEOTIDE PROBES FOR DETECTION AND QUANTITATION OF CANDIDA SPECIES

(75) Inventors: James J. Hogan, Coronado, CA (US); Patricia C. Gordon, Spring Valley, CA (US)

(73) Assignee: Gen-Probe, Incorporated, San Diego, CA (US)

( * ) Notice: Subject to any disclaimer, the term of this patent is extended or adjusted under 35 U.S.C. 154(b) by 0 days.

(21) Appl. No.: 09/846,797

(22) Filed: May 1, 2001

(65) Prior Publication Data

US 2003/0165833 A1 Sep. 4, 2003

Related U.S. Application Data

(60) Provisional application No. 60/201,249, filed on May 1, 2000.

(51) Int. Cl.[7] .......................... C12Q 1/68; C12N 12/74; C07H 21/02; C07H 21/04
(52) U.S. Cl. .......................... 435/6; 435/471; 536/23.1
(58) Field of Search .............................. 536/23.1; 435/6

(56) References Cited

U.S. PATENT DOCUMENTS

| | | |
|---|---|---|
| 5,403,710 A | 4/1995 | Weisburg et al. |
| 5,426,027 A | 6/1995 | Lott et al. |
| 5,541,308 A | 7/1996 | Hogan et al. |
| 5,545,525 A | 8/1996 | Montplaisir et al. |
| 5,580,971 A | 12/1996 | Mitsuhashi |
| 5,631,132 A | 5/1997 | Lott et al. |
| 5,635,353 A | 6/1997 | Lott et al. |
| 5,639,612 A | 6/1997 | Mitsuhashi et al. |
| 5,645,992 A | 7/1997 | Lott et al. |
| 5,688,644 A | 11/1997 | Lott et al. |
| 6,017,699 A | 1/2000 | Jordan |

FOREIGN PATENT DOCUMENTS

| | | |
|---|---|---|
| EP | 0982298 A1 | 3/2000 |
| WO | WO 00/73499 A2 | 12/2000 |

OTHER PUBLICATIONS

Barns et al., "Evolutionary Relationships among Pathogenic Candida Species and Relatives", Journal of Bacteriology, vol. 173, No. 7, p. 2250–2255, Apr. 1991.

Fujita et al., "Microtitration Plate Enzyme Immunoassay To Detect PCR–Amplified DNA from Candida Species in Blood", Journal of Clinical Microbiology, vol. 33, No. 4, p. 962–967, Apr. 1995.

Lischewski et al., "Specific detection of Candida albicans and Candida tropicalis by fluorescent in situ hybridization with an 18s rRNA–targeted oligonucleotide probe", Microbiology, vol. 142, p. 2731–2740, 1996*.

Sullivan et al., "Molecular genetic approaches to identification, epidemiology and taxonomy of non–albicans Candida species", J. Med Microbiol., vol. 44, p. 399–408, 1996*.

Lischewski et al., "Detection and Identification of Candida Species in Experimentally Infected Tissue and Human Blood by rRNA–Specific Fluorescent In Situ Hybridization", Journal of Clinical Microbiology, vol. 35, No. 11, p. 2943–2948, Nov. 1997.

Gilfillan et al., "Candida dubliniensis: phylogeny and putative virulence factors", Microbiology, p. 829–838, 1998*.

Elie et al., "Rapid Identification of Candida Species with Species–Specific DNA Probes", Journal of Clinical Microbiology, vol. 36, No. 11, p. 3260–3265, Nov. 1998.

Shin et al., "Rapid Identification of up to Three Candida Species in a Single Reaction Tube by a 5' Exonuclease Assay Using Fluorescent DNA Probes", Journal of Clinical Microbiology, vol. 37, No. 11, p. 165–170, Jan. 1999.

Camaioni et al., "Deoxyadenosine Bisphosphate Derivatives as Potent Antagonists at P2Y1 Receptors", J Med Chem, Jan. 1998, 41(2):183–90.

Sullivan, "18S Ribosomal RNA; 18S rRNA Gene", EBI Online—EMBL Release CD18SRRNA (X99399), Jan. 1997.

WIDJOJOATMODJO et al., "Nucleic Acid Sequence–based Amplification (NASBA) Detection of Medically Important Candida Species", J Microbiol Methods, Oct. 1999, 38(1–2):81–90.

Primary Examiner—James Ketter
Assistant Examiner—Konstantina Katcheves
(74) Attorney, Agent, or Firm—Michael J. Gilly

(57) ABSTRACT

Hybridization probes and accessory oligonucleotides useful for detecting ribosomal nucleic acids from Candida albicans, Candida tropicalis, Candida dubliniensis, Candida viswanathii and Candida parapsilosis with high specificity.

25 Claims, No Drawings

POLYNUCLEOTIDE PROBES FOR DETECTION AND QUANTITATION OF CANDIDA SPECIES

RELATED APPLICATION

This application claims the benefit of U.S. Provisional Application No. 60/201,249, filed May 1, 2000. The entire disclosure of this related application is hereby incorporated by reference.

FIELD OF THE INVENTION

The present invention relates to compositions and methods for detecting one or more species of yeast in the genus Candida. More specifically, the invention relates to hybridization probes and accessory polynucleotides having specificity for ribosomal nucleic acids from a defined collection of Candida species.

BACKGROUND OF THE INVENTION

Candida spp. are frequently present as members of the normal flora of the mouth, throat, large intestine, vagina, and skin and are often contaminates in exudates or other specimens taken from these areas. In patients whose immune defenses have been compromised by disease or by the secondary effects of drugs used to treat their diseases, microorganisms that are part of the normal flora may invade deeper tissues and produce life-threatening infections. *Candida albicans* (*C. albicans*), the principal pathogenic species, causes mild to severe or chronic superficial infections of the skin, nails and mucous membranes in individuals with normal immune defenses, as well as serious systemic infections in debilitated patients. *Candida parapsilosis, C. tropicalis*, and *C. guilliermondii* have become important causes of endocarditis, pyelonephritis, arthritis, and disseminated candidaisis in patients with indwelling intravenous catheters, patients undergoing cardiovascular surgery, and drug addicts. (see *Manual of Clinical Microbiology*, 4th Edition, (1985) Lennette et al. (eds.), American Association for Microbiology, Washington, D.C., p. 535)

It is well established that two single strands of deoxyribonucleic acid ("DNA") or ribonucleic acid ("RNA") can associate or "hybridize" with one another to form a double-stranded structure having two strands held together by hydrogen bonds between complementary base pairs. The individual strands of nucleic acid are formed from nucleotides that comprise the bases: adenine (A), cytosine (C), thymine (T), guanine (G), uracil (U) and inosine (I). In the double helical structure of nucleic acids, the base adenine hydrogen bonds with the base thymine or uracil, the base guanine hydrogen bonds with the base cytosine and the base inosine hydrogen bonds with adenine, cytosine or uracil. At any point along the chain, therefore, one may find the classical "Watson-Crick" base pairs A:T or A:U, T:A or U:A, and G:C or C:G. However, one may also find A:G, G:U and other "wobble" or mismatched base pairs in addition to the traditional ("canonical") base pairs.

A double-stranded nucleic acid hybrid will result if a first single-stranded polynucleotide is contacted under hybridization-promoting conditions with a second single-stranded polynucleotide having a sufficient number of contiguous bases complementary to the sequence of the first polynucleotide. DNA/DNA, RNA/DNA or RNA/RNA hybrids may be formed under appropriate conditions.

Generally, a probe is a single-stranded polynucleotide having some degree of complementarity with the nucleic acid sequence that is to be detected ("target sequence"). Probes commonly are labeled with a detectable moiety such as a radioisotope, an antigen or a chemiluminescent moiety.

Descriptions of nucleic acid hybridization as a procedure for detecting particular nucleic acid sequences are given by Kohne in U.S. Pat. No. 4,851,330, and by Hogan et al., in U.S. Pat. Nos. 5,541,308 and 5,681,698. These references also describe methods for determining the presence of RNA-containing organisms in a sample which might contain such organisms. These procedures require probes that are sufficiently complementary to the ribosomal RNA (rRNA) of one or more non-viral organisms or groups of non-viral organisms. According to the method, nucleic acids from a sample to be tested and an appropriate probe are first mixed and then incubated under specified hybridization conditions. Conventionally, but not necessarily, the probe will be labeled with a detectable label. The resulting hybridization reaction is then assayed to detect and quantitate the amount of labeled probe that has formed duplex structures in order to detect the presence of rRNA contained in the test sample.

With the exception of viruses, all prokaryotic organisms contain rRNA genes encoding homologs of the procaryotic 5S, 16S and 23S rRNA molecules. In eucaryotes, these rRNA molecules are the 5S rRNA, 5.8S rRNA, 18S rRNA and 28S rRNA which are substantially similar to the prokaryotic molecules. Probes for detecting specifically targeted rRNA subsequences in particular organisms or groups of organisms in a sample have been described previously. These highly specific probe sequences advantageously do not substantially cross react with nucleic acids from other fungal species or infectious agents under appropriate stringency conditions.

The present invention provides polynucleotide probes that can be used to detect *Candida albicans, Candida tropicalis, Candida dubliniensis, Candida viswanathii* and *Candida parapsilosis* in a highly specific manner.

SUMMARY OF THE INVENTION

A first aspect of the invention relates to an oligonucleotide having a sequence that is up to 100 nucleotides in length, and that includes at least 26 contiguous nucleotides contained within the sequence of SEQ ID NO:7 or the complement thereof. Preferably, the sequence of the oligonucleotide includes any one of SEQ ID NO:1 or the complement thereof, SEQ ID NO:2 or the complement thereof, SEQ ID NO:3 or the complement thereof, SEQ ID NO:4 or the complement thereof, SEQ ID NO:5 or the complement thereof, and SEQ ID NO:6 or the complement thereof. Even more preferably, the length of the oligonucleotide is up to 60 nucleotides. According to one embodiment of the invention, the oligonucleotide is made of DNA. According to a different embodiment, the oligonucleotide includes at least one nucleotide analog. For example, the nucleotide analog may have a methoxy group at the 2' position of a ribose moiety. According to yet another embodiment, the sequence of the oligonucleotide consists of any one of SEQ ID NO:1 or the complement thereof, SEQ ID NO:2 or the complement thereof, SEQ ID NO:3 or the complement thereof, SEQ ID NO:4 or the complement thereof, SEQ ID NO:5 or the complement thereof, and SEQ ID NO:6 or the complement thereof. When this is the case, the oligonucleotide may further include a detectable label. Alternatively, the sequence of the oligonucleotide may be given by either SEQ ID NO:1 or SEQ ID NO:5. In a preferred embodiment, the oligonucleotide further includes a detectable label, which may be a chemiluminescent label. A particular example of a chemiluminescent label would be an acridinium ester.

A second aspect of the invention relates to a composition that is useful for detecting the nucleic acids of a yeast that is any of *C. albicans, C. tropicalis, C. dubliniensis, C. viswanathii* and *C. parapsilosis*. The invented composition includes an oligonucleotide probe having a length of up to 100 nucleotide bases and a sequence that includes the sequence of SEQ ID NO:1 or the complement thereof. According to one embodiment, the length of the oligonucleotide probe is up to 60 nucleotides. Preferably, the oligonucleotide probe includes a detectable label. According to another embodiment, the oligonucleotide probe is made of DNA. According to still another embodiment, the sequence of the oligonucleotide probe is given by SEQ ID NO:1. When this is the case, the oligonucleotide probe may further include a detectable label, such as a chemiluminescent label or a radiolabel. According to a preferred embodiment, when the sequence of the oligonucleotide is given by SEQ ID NO:1, and when the oligonucleotide includes a detectable label, the detectable label may be a chemiluminescent label or a radiolabel. According to a highly preferred embodiment, the detectable label is a chemiluminescent label, and the chemiluminescent label is an acridinium ester. Alternatively, when the sequence of the oligonucleotide is given by SEQ ID NO:1, and when the oligonucleotide includes a detectable label, the composition may further include at least one helper oligonucleotide. According to one preferred embodiment, the helper oligonucleotide can have a sequence selected from the group consisting of SEQ ID NO:2, SEQ ID NO:3 and SEQ ID NO:4. According to a different preferred embodiment, the helper oligonucleotide includes at least one nucleotide analog. When this is the case, the nucleotide analog may include a ribose moiety having a methoxy group disposed at the 2' position.

A third aspect of the invention relates to a method for determining whether an organism in the genus Candida is present in a test sample. According to the invented method, there is a first step for providing to the test sample a probe composition that includes an oligonucleotide probe having a length of up to 100 nucleotide bases and including the sequence of SEQ ID NO:1. A second step in the method involves hybridizing under a high stringency condition any nucleic acid that may be present in the test sample with the probe composition to form a probe:target duplex. Finally, there is a third step for detecting the probe:target duplex as an indicator of the presence of an organism that is any of *C. albicans, C. tropicalis, C. dubliniensis, C. viswanathii* and *C. parapsilosis* in the test sample. According to one embodiment, the sequence of the oligonucleotide probe in the first step of the method consists of SEQ ID NO:1. When this is the case, the test sample may comprise yeast cells, and before the first step there is a preliminary step for releasing nucleic acid from any yeast cells that may be present in the test sample. Alternatively, when the oligonucleotide probe used in the detection method has the sequence of SEQ ID NO:1 or SEQ ID NO: 5, it is preferred that the oligonucleotide probe includes a detectable label. An example of such a detectable label would be an acridinium ester, whereby any probe:target duplex could be detected by luminometry. According to still another preferred embodiment, when the oligonucleotide probe has the sequence of either SEQ ID NO:1 or SEQ ID NO:5 and includes a detectable label, the probe composition may further include at least one helper oligonucleotide. For example, the helper oligonucleotide may be any of SEQ ID NO:2, SEQ ID NO:3 or SEQ ID NO:4. In a particular example of the invented method, the oligonucleotide probe in the first step has the sequence of SEQ ID NO:1, and the helper oligonucleotide has a sequence selected from the group of SEQ ID NO:2 and SEQ ID NO:4. In some embodiments of the invention, the test sample used in the detection method is a lysate. Generally speaking, examples of high stringency conditions useful in connection with the invented method can be provided by: (a) 0.48 M sodium phosphate buffer, 0.1% sodium dodecyl sulfate, 1 mM each of EDTA and EGTA; or (b) 0.6 M LiCl, 1% lithium lauryl sulfate, 60 mM lithium succinate and 10 mM each of EDTA and EGTA.

A fourth aspect of the invention relates to a kit for detecting the presence of nucleic acids from any of *C. albicans, C. tropicalis, C. dubliniensis, C. viswanathii* and *C. parapsilosis* in a test sample. The kit includes a composition which itself includes a labeled oligonucleotide probe having the sequence of SEQ ID NO:1. Also included in the kit is at least one helper oligonucleotide. These helper oligonucleotides could, for example, have the sequence of any of SEQ ID NO:2, SEQ ID NO:3 or SEQ ID NO:4.

Definitions

As used herein, the following terms have the given meanings unless expressly stated to the contrary.

A "nucleotide" is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The sugar of a 5'-nucleotide contains a hydroxyl group (—OH) at the 5'-carbon-5 position. The term also includes analogs of naturally occurring nucleotides and particularly includes analogs having a methoxy group at the 2' position of the ribose (OMe). As used herein, methoxy oligonucleotides containing "T" residues have a methoxy group at the 2' position of the ribose moiety, and a uracil at the base position of the nucleotide. When particularly specified as "OMeT" it is meant that the base position of the nucleotide is occupied by a thymine residue.

A "non-nucleotide unit" is a unit which does not significantly participate in hybridization of a polymer. Such units must not, for example, participate in any significant hydrogen bonding with a nucleotide, and would exclude units having as a component one of the five nucleotide bases or analogs thereof.

An "oligonucleotide" is a nucleotide polymer having two or more nucleotide subunits covalently joined together. Oligonucleotides are generally about 10 to about 100 nucleotides in length. The sugar groups of the nucleotide subunits may be ribose, deoxyribose, or modified derivatives thereof such as OMe. The nucleotide subunits may by joined by linkages such as phosphodiester linkages, modified linkages or by non-nucleotide moieties that do not prevent hybridization of the oligonucleotide to its complementary target nucleotide sequence. Modified linkages include those in which a standard phosphodiester linkage is replaced with a different linkage, such as a phosphorothioate linkage, a methylphosphonate linkage, or a neutral peptide linkage. Nitrogenous base analogs also may be components of oligonucleotides in accordance with the invention.

A "target nucleic acid" is a nucleic acid comprising a target nucleic acid sequence.

A "target nucleic acid sequence," "target nucleotide sequence" or "target sequence" is a specific deoxyribonucleotide or ribonucleotide sequence that can be hybridized by an oligonucleotide.

An "oligonucleotide probe" is an oligonucleotide having a nucleotide sequence sufficiently complementary to its target nucleic acid sequence to be able to form a detectable hybrid probe:target duplex under high stringency hybridization conditions. An oligonucleotide probe is an isolated chemical species and may include additional nucleotides outside of the targeted region as long as such nucleotides do not prevent hybridization under high stringency hybridization conditions. Non-complementary sequences, such as promoter sequences, restriction endonuclease recognition sites, or sequences that confer a desired secondary or tertiary structure such as a catalytic active site can be used to facilitate detection using the invented probes. An oligonucleotide probe optionally may be labeled with a detectable moiety such as a radioisotope, a fluorescent moiety, a chemiluminescent moiety, an enzyme or a ligand, which can be used to detect or confirm probe hybridization to its target sequence. Oligonucleotide probes are preferred to be in the size range of from 10 to 100 nucleotides in length.

A "detectable moiety" is a molecule attached to, or synthesized as part of a nucleic acid probe. This molecule should be uniquely detectable and will allow the probe to be detected as a result. These detectable moieties are often radioisotopes, chemiluminescent molecules, enzymes, haptens, or even unique oligonucleotide sequences.

A "hybrid" or a "duplex" is a complex formed between two single-stranded nucleic acid sequences by Watson-Crick base pairings or non-canonical base pairings between the complementary bases.

"Hybridization" is the process by which two complementary strands of nucleic acid combine to form a double-stranded structure ("hybrid" or "duplex").

"Complementarity" is a property conferred by the base sequence of a single strand of DNA or RNA which may form a hybrid or double-stranded DNA:DNA, RNA:RNA or DNA:RNA through hydrogen bonding between Watson-Crick base pairs on the respective strands. Adenine (A) ordinarily complements thymine (T) or Uracil (U), while guanine (G) ordinarily complements cytosine (C).

"Mismatch" refers to any pairing, in a hybrid, of two nucleotides which do not form canonical Watson-Crick hydrogen bonds. In addition, for the purposes of the following discussions, a mismatch can include an insertion or deletion in one strand of the hybrid which results in an unpaired nucleotide(s).

The term "stringency" is used to describe the temperature and solvent composition existing during hybridization and the subsequent processing steps. Under high stringency conditions only highly complementary nucleic acid hybrids will form; hybrids without a sufficient degree of complementarity will not form. Accordingly, the stringency of the assay conditions determines the amount of complementarity needed between two nucleic acid strands forming a hybrid. Stringency conditions are chosen to maximize the difference in stability between the hybrid formed with the target and the non-target nucleic acid. Exemplary high stringency conditions are provided in the working examples.

The term "probe specificity" refers to a characteristic of a probe which describes its ability to distinguish between target and non-target sequences.

The term "variable region" refers to a nucleotide polymer which differs by at least one base between the target organism and non-target organisms contained in a sample.

A "conserved region" is a nucleic acid subsequence which is not variable between at least two different polynucleotides.

The term "sequence divergence" refers to a process by which nucleotide polymers become less similar during evolution.

The term "sequence convergence" refers to a process by which nucleotide polymers become more similar during evolution.

"Tm" refers to the temperature at which 50% of the probe is converted from the hybridized to the unhybridized form.

A "helper oligonucleotide" is an oligonucleotide that binds a region of a target nucleic acid other than the region that is bound by an oligonucleotide probe. Helper oligonucleotides impose new secondary and tertiary structures on the targeted region of the single-stranded nucleic acid so that the rate of binding of the oligonucleotide probe is accelerated. Although helper oligonucleotides are not labeled with a detectable label when used in conjunction with labeled oligonucleotide probes, they facilitate binding of labeled probes and so indirectly enhance hybridization signals.

The phrases "consist essentially of" or "consisting essentially of" means that the oligonucleotide has a nucleotide sequence substantially similar to a specified nucleotide sequence. Any additions or deletions are non-material variations of the specified nucleotide sequence which do not prevent the oligonucleotide from having its claimed property, such as being able to preferentially hybridize under high stringency hybridization conditions to its target nucleic acid over non-target nucleic acids.

One skilled in the art will understand that substantially corresponding probes of the invention can vary from the referred-to sequence and still hybridize to the same target nucleic acid sequence. This variation from the nucleic acid may be stated in terms of a percentage of identical bases within the sequence or the percentage of perfectly complementary bases between the probe and its target sequence. Probes of the present invention substantially correspond to a nucleic acid sequence if these percentages are from 100% to 80% or from 0 base mismatches in a 10 nucleotide target sequence to 2 bases mismatched in a 10 nucleotide target sequence. In preferred embodiments, the percentage is from 100% to 85%. In more preferred embodiments, this percentage is from 90% to 100%; in other preferred embodiments, this percentage is from 95% to 100%.

By "sufficiently complementary" or "substantially complementary" is meant nucleic acids having a sufficient amount of contiguous complementary nucleotides to form, under high stringency hybridization conditions, a hybrid that is stable for detection.

By "nucleic acid hybrid" or "probe:target duplex" is meant a structure that is a double-stranded, hydrogen-bonded structure, preferably 10 to 100 nucleotides in length, more preferably 14 to 50 nucleotides in length. The structure is sufficiently stable to be detected by means such as chemiluminescent or fluorescent light detection, autoradiography, electrochemical analysis or gel electrophoresis. Such hybrids include RNA:RNA, RNA:DNA, or DNA:DNA duplex molecules.

By "negative sense" is meant a nucleic acid molecule perfectly complementary to a reference (i.e., sense) nucleic acid molecule.

"RNA and DNA equivalents" refer to RNA and DNA molecules having the same complementary base pair hybridization properties. RNA and DNA equivalents have different sugar groups (i.e., ribose versus deoxyribose), and may differ by the presence of uracil in RNA and thymine in DNA. The difference between RNA and DNA equivalents do not contribute to differences in substantially corresponding nucleic acid sequences because the equivalents have the same degree of complementarity to a particular sequence.

By "preferentially hybridize" is meant that under high stringency hybridization conditions oligonucleotide probes can hybridize their target nucleic acids to form stable probe:target hybrids (thereby indicating the presence of the target nucleic acids) without forming stable probe:non-target hybrids (that would indicate the presence of non-target nucleic acids from other organisms). Thus, the probe hybridizes to target nucleic acid to a sufficiently greater extent than to non-target nucleic acid to enable one skilled in the art to accurately detect the presence of Candida albicans, Candida tropicalis, Candida dubliniensis, Candida viswanathii and Candida parapsilosis and distinguish their presence from that of other organisms. Preferential hybridization can be measured using techniques known in the art and described herein.

A "target nucleic acid sequence region" refers to a nucleic acid sequence present in the nucleic acid of an organism or a sequence complementary thereto, which is not present in the nucleic acids of other species. Nucleic acids having nucleotide sequences complementary to a target sequence may be generated by target amplification techniques such as polymerase chain reaction (PCR) or transcription mediated amplification (e.g., Kacian and Fultz, Nucleic Acid Sequence Amplification Methods, U.S. Pat. No. 5,824,518).

DETAILED DESCRIPTION OF THE INVENTION

Herein we disclose preferred target nucleotide sequences for oligonucleotide probes and helper oligonucleotides that can be used to detect and identify rRNA or rDNA of Candida albicans, Candida tropicalis, Candida dubliniensis, Candida viswanathii and Candida parapsilosis without substantially detecting ribosomal nucleic acids of other microorganisms or humans. Highly preferred polynucleotide probes and accessory helper oligonucleotides that are useful for specifically detecting Candida albicans, Candida tropicalis, Candida dubliniensis, Candida viswanathii and Candida parapsilosis are particularly disclosed. The probes, which are complementary to particular rRNA sequences of the 18S rRNA, advantageously are capable of distinguishing these Candida species from the known phylogenetically nearest neighbors.

In addition to having nucleic acid sequences that permit hybridization to the ribosomal RNA (rRNA) or DNA (rDNA) sequences of the indicated Candida species, the oligonucleotide probes of the invention are at least 90% complementary, preferably perfectly complementary, to at least a portion of the described RNA target sequence region identified by SEQ ID NO:8. The desired portion is preferably at least 15 nucleotides, still more preferably at least 26 nucleotides, even more preferably at least 28 nucleotides, and still even more preferably 29 nucleotides in length.

As stated above, the invented oligonucleotides are targeted to nucleic acid sequences of Candida albicans, Candida tropicalis, Candida dubliniensis, Candida viswanathii and Candida parapsilosis. These oligonucleotides can be used as probes that preferentially hybridize a ribosomal nucleic acid target region to form a detectable duplex that indicates the presence of at least one of these Candida species. Alternatively, the invented oligonucleotides can be used as helper oligonucleotides that hybridize to a ribosomal nucleic acid target region under high stringency hybridization conditions, and that can enhance the formation of a duplex between a labeled oligonucleotide probe and its complementary target nucleic acid.

In preferred embodiments, the oligonucleotide probes described herein selectively hybridize nucleic acids from Candida albicans, Candida tropicalis, Candida dubliniensis, Candida viswanathii and Candida parapsilosis over those from other organisms under high stringency hybridization conditions. In some embodiments of the present invention, the oligonucleotide probe comprises a detectable moiety, such as an acridinium ester or a radioisotope.

Preferred methods for detecting the presence of Candida albicans, Candida tropicalis, Candida dubliniensis, Candida viswanathii and Candida parapsilosis include the step of contacting a test sample under high stringency hybridization conditions with an oligonucleotide probe that preferentially hybridizes to a target ribosomal nucleic acid sequence from this subgroup of Candida species over a nucleic acid sequence of other organisms.

Preferred oligonucleotides in accordance with the invention have sequences of up to 100 nucleotides in length and are fully complementary to a sequence of at least 15 contiguous nucleotides, more preferably at least 26 contiguous nucleotides, still more preferably at least 28 contiguous nucleotides, and yet still more preferably at least 29 contiguous nucleotides contained in the sequence given by SEQ ID NO:8. Those oligonucleotides may be made of DNA, RNA or analogs of these polynucleotides provided that they hybridize to the stated sequences. Some oligonucleotides useful for hybridizing Candida ribosomal nucleic acids preferably are up to 100 nucleotides in length and have at least 15 contiguous nucleotides, more preferably at least 26 contiguous nucleotides, still more preferably at least 28 contiguous nucleotides, and yet still more preferably at least 29 contiguous nucleotides contained in the sequence given by SEQ ID NO:7.

With respect to preferred lengths, oligonucleotides according to the invention preferably have lengths of up to 100 nucleotides, or more preferably up to 60 nucleotides. Of course, it is particularly preferred for oligonucleotides to have the precise lengths and sequences which are disclosed herein. Since either strand of a ribosomal nucleic acid may be targeted by the oligonucleotides, complements of the oligonucleotides described in the procedures appearing below also can be used for detecting and quantifying the ribosomal nucleic acids of Candida species.

Introduction and Background

In the development of the invention, rRNA sequences from a collection of related and unrelated organisms were aligned to identify candidate conserved sequences present in the 18S rRNA that could be used to distinguish Candida albicans, Candida tropicalis, Candida dubliniensis, Candida viswanathii and Candida parapsilosis from other organisms. The rRNA or rDNA sequences of Candida albicans, Candida tropicalis and Candida parapsilosis, together with distant phylogenetic neighbors were aligned to reveal areas of maximum homology. Homologous regions were examined for sequence variation in order to identify rRNA sequences that were conserved among the desired Candida species and that showed mismatches with other closely and distantly related genera. The sequences deduced as candidate probes according to the methods described below finally were tested against a panel of rRNA standards and fungal lysates to verify their utility as probes under laboratory conditions.

Polynucleotide sequences of rRNAs are most conveniently determined using a dideoxynucleotide sequencing procedure. In this procedure, oligonucleotide primers of about 10–100 bases in length and complementary to conserved regions of rRNA from any of the ribosome subunits can be extended by reverse transcriptase. The resulting DNA extension products can then be sequenced either by chemical degradation or by dideoxynucleotide sequencing (Lane et al., Proc. Natl. Acad. Sci. USA 82: 6955 (1985)). According to another preferred method, genomic sequences encoding the rRNA can also be determined.

The strong interdependence of secondary structure and function of the rRNA molecules is well known. Indeed, evolutionary changes in the primary sequence of the rRNA are effectively restricted such that secondary structure of the molecule will be maintained. For example, if a base is changed on one side of a helix of a rRNA molecule, then a compensating change will be made on the other side of the helix to preserve complementarity (this is referred to as covariance). This relationship allows two very different rRNA sequences to be "aligned" based on conserved primary sequence and conserved elements of the secondary structure. Once the sequences have been aligned, it becomes possible to identify conserved and variable regions of the rRNA sequence.

Variable regions of rRNAs were identified by comparative analysis using published rRNA sequences and sequences that were determined during the development of the present invention. Commercially available software can be used or adapted for the purposes disclosed herein. Since the sequence evolution at each of the variable regions (for example, spanning a minimum of 10 nucleotides) of rRNA is, for the most part, divergent and not convergent, we can confidently design probes based on a few rRNA sequences which differ between the target organism and its phylogenetically closest relatives.

Probe Selection Guidelines

The following general guidelines can be used for designing probes having desirable characteristics in accordance with the present invention. Manipulation of one or more of the many factors that influence the extent and specificity of a hybridization reaction can determine the sensitivity and specificity of a particular probe. This is true whether or not the probe is perfectly complementary over the full length of its target polynucleotide sequence. Guidelines for preparing probes useful in connection with the invention now follow.

First, the stability of the probe:target nucleic acid hybrid should be chosen to be compatible with the assay conditions. This may be accomplished by avoiding long A and T rich sequences, by terminating the hybrids with G:C base pairs and by designing the probe in such a way that the Tm will be appropriate for standard conditions to be employed in the assay. The nucleotide sequence of the probe should be chosen so that the length and %G and %C result in a probe having a Tm about 2–10° C. higher than the temperature at which the final assay will be performed. The base composition of the probe is significant because G:C base pairs exhibit greater thermal stability when compared with A:T base pairs. Thus, hybrids involving complementary nucleic acids having a high G:C content will be stable at higher temperatures when compared with hybrids having a lower G:C content.

Ionic strength and temperature conditions at which a hybridization reaction will be conducted also should be considered when designing a probe having a negatively charged backbone, such as would be provided by phosphodiester linkages between nucleotides. It is generally known that hybridization rate increases as ionic strength of the reaction mixture increases. Similarly, the thermal stability of hybrids increases with increasing ionic strength. Conversely, hydrogen bond-disrupting reagents such as formamide, urea, DMSO and alcohols increase the stringency of hybridization. Destabilization of hydrogen bonds by reagents in this class can greatly reduce the Tm. In general, optimal hybridization for synthetic oligonucleotide probes of about 10–50 bases in length occurs approximately 5° C. below the melting temperature for a given duplex. Hybridization reactions conducted below the temperature optimum may allow mismatched base sequences to hybridize and can result in reduced probe specificity.

Second, the position at which the probe binds its target polynucleotide should be chosen to minimize the stability of hybrids formed between probe:non-target polynucleotides. This may be accomplished by minimizing the length of perfect complementarity with polynucleotides of non-target organisms, by avoiding G:C rich regions of homology with non-target sequences, and by positioning the probe to span as many destabilizing mismatches as possible. Whether a probe sequence will be useful for detecting only a specific type of organism depends largely on thermal stability differences between probe:target hybrids and probe:non-target hybrids. The differences in Tm should be as large as possible to produce highly specific probes.

The length of the target nucleic acid sequence and the corresponding length of the probe sequence also are important factors to be considered when designing a probe useful for specifically detecting *Candida albicans, Candida tropicalis, Candida dubliniensis, Candida viswanathii* and *Candida parapsilosis*. While it is possible for polynucleotides that are not perfectly complementary to hybridize to each other, the longest stretch of perfectly homologous base sequence will ordinarily be the primary determinant of hybrid stability.

Third, regions of the rRNA which are known to form strong internal structures inhibitory to hybridization of a probe are less preferred as targets. Probes having extensive self-complementarity also should be avoided. As indicated above, hybridization is the association of two single strands of complementary nucleic acid to form a hydrogen bonded double-stranded structure. If one of the two strands is wholly or partially double-stranded, then it will be less able to participate in the formation of a new hybrid. Significantly, all rRNA molecules form very stable intramolecular hybrids.

The rate and extent of hybridization between a probe and its target can be increased substantially by designing the probe such that a substantial portion of the sequence of interest is single-stranded. If the target nucleic acid to be detected is a genomic sequence encoding a rRNA, then that target will naturally occur in a double-stranded form. This is also the case with products of the polymerase chain reaction (PCR). These double-stranded targets are naturally inhibitory to hybridization with a probe. Finally, undesirable intramolecular and intermolecular hybrids can form within a single probe molecule or between different probe molecules if there is sufficient self-complementarity. Thus, extensive self-complementarity in a probe sequence should be avoided.

Preferably, probes useful for carrying out the procedures described below will hybridize only under conditions of high stringency. Under these conditions only highly complementary nucleic acid hybrids will form (i.e., those having at least 14 out of 17 bases in a contiguous series of bases being complementary). Hybrids will not form in the absence of a sufficient degree of complementarity. Accordingly, the stringency of the assay conditions determines the amount of complementarity needed between two nucleic acid strands forming a hybrid. Stringency is chosen to maximize the difference in stability between the hybrid formed with the target and non-target nucleic acid. Exemplary high stringency conditions are employed in the Examples presented below.

While oligonucleotide probes of different lengths and base composition may be used for detecting *Candida albicans, Candida tropicalis, Candida dubliniensis, Candida viswanathii* and *Candida parapsilosis*, preferred probes in this invention have lengths of up to 100 nucleotides, and more preferably lengths of up to 60 nucleotides. Preferred length ranges for the invented oligonucleotides are from 10 to 100 bases in length, more preferably between 15 and 60 bases in length, or still more preferably between 15 and 50 bases in length and are sufficiently homologous to the target nucleic acid to permit hybridization under high stringency conditions such as those employed in the Examples described below. However, the specific probe sequences described below also may be provided in a nucleic acid cloning vector or transcript or other longer nucleic acid and still can be used for detecting *Candida albicans, Candida tropicalis, Candida dubliniensis, Candida viswanathii* and *Candida parapsilosis* in a highly specific manner.

Chemical Structure of Oligonucleotides

All of the oligonucleotides of the present invention may be modified with chemical groups to enhance their performance. Thus, it is to be understood that references to "oligonucleotide probes" or "helper oligonucleotides" or simply "oligonucleotides" embrace polymers of native nucleotides as well as polymers that include at least one nucleotide analog.

Backbone-modified oligonucleotides, such as those having phosphorothioate or methylphosphonate groups, are examples of analogs that can be used in conjunction with oligonucleotides of the present invention. These modifications render the oligonucleotides resistant to the nucleolytic activity of certain polymerases or nuclease enzymes. Other analogs that can be incorporated into the structures of the oligonucleotides disclosed herein include peptide nucleic acids, or "PNAs." The PNAs are compounds comprising ligands linked to a peptide backbone rather than to a phosphodiester backbone. Representative ligands include either the four main naturally occurring DNA bases (i.e., thymine, cytosine, adenine or guanine) or other naturally occurring nucleobases (e.g., inosine, uracil, 5-methylcytosine or thiouracil) or artificial bases (e.g., bromothymine, azaadenines or azaguanines, etc.) attached to a peptide backbone through a suitable linker. The PNAs are able to bind complementary ssDNA and RNA strands. Methods for making and using PNAs are disclosed in U.S. Pat. No. 5,539,082. Another type of modification that can be used to make oligonucleotides having the sequences described herein involves the use of non-nucleotide linkers (e.g., Arnold, et al., "Non-Nucleotide Linking Reagents for Nucleotide Probes", U.S. Pat. No. 6,031,091 hereby incorporated by reference) incorporated between nucleotides in the nucleic acid chain which do not interfere with hybridization or the elongation of a primer.

Nucleic Acid Based Methods of Detecting rRNA or rDNA

A composition that includes an oligonucleotide probe, either alone or in combination with one or more helper oligonucleotides, can be used for detecting rRNA or rDNA of *Candida albicans, Candida tropicalis, Candida dubliniensis, Candida viswanathii* and *Candida parapsilosis* in a hybridization assay. Defined oligonucleotides that can be used to practice the invention can be produced by any of several well-known methods, including automated solid-phase chemical synthesis using cyanoethylphosphoramidite precursors (Barone et al., *Nucl Acids Res* 12:4051 (1984)). Other well-known methods for preparing synthetic oligonucleotides also may be employed.

Essentially any labeling and detection system that can be used for monitoring specific nucleic acid hybridization can be used in conjunction with the probes disclosed herein when a labeled probe is desired. Included among the collection of useful labels are: isotopic labels, enzymes, haptens, linked oligonucleotides, chemiluminescent molecules and redox-active moieties that are amenable to electrochemical detection methods. Standard isotopic labels that can be used to produce labeled oligonucleotides include $^{3}$H, $^{35}$S, $^{32}$P, $^{125}$I, $^{57}$Co and $^{14}$C. When using radiolabeled probes, hybrids can be detected by autoradiography, scintillation counting or gamma counting.

Non-isotopic materials can also be used for labeling oligonucleotide probes. These non-isotopic labels can be positioned internally or at a terminus of the oligonucleotide probe. Modified nucleotides may be incorporated enzymatically or chemically with modifications of the probe being performed during or after probe synthesis, for example, by the use of non-nucleotide linker groups. Non-isotopic labels include fluorescent molecules, chemiluminescent molecules, enzymes, cofactors, enzyme substrates, haptens or other ligands.

Indeed, any number of different non-isotopic labels can be used for preparing labeled oligonucleotides in accordance with the invention. Preferred chemiluminescent molecules include acridinium esters of the type disclosed by Arnold et al., in U.S. Pat. No. 5,283,174 for use in connection with homogenous protection assays, and of the type disclosed by Woodhead et al., in U.S. Pat. No. 5,656,207 for use in connection with assays that quantify multiple targets in a single reaction. The disclosures contained in these patent documents are hereby incorporated by reference. U.S. Pat. 5,998,135 discloses yet another method that can be used for labeling and detecting the probes of the present invention using fluorimetry to detect fluorescence emission from lanthanide metal labels disposed on probes, where the emission from these labels becomes enhanced when it is in close proximity to an energy transfer partner. Preferred electrochemical labeling and detection approaches are disclosed in U.S. Pat. Nos. 5,591,578 and 5,770,369, and the published International Patent Application No. PCT/US98/12082, the disclosures of which are hereby incorporated by reference. Redox active moieties useful as electrochemical labels in the present invention include transition metals such as Cd, Mg, Cu, Co, Pd, Zn, Fe and Ru.

Those having an ordinary level of skill in the art will appreciate that alternative procedures for detecting nucleic acids of Candida species using the invented probes can be carried out using either labeled probes or unlabeled probes. For example, hybridization assay methods that do not rely on the use of a labeled probe are disclosed in U.S. Pat. No. 5,945,286 which describes immobilization of unlabeled probes made of peptide nucleic acids (PNAs), and detectably labeled intercalating molecules which can bind double-stranded PNA probe/target nucleic acid duplexes. In these procedures, as well as in certain electrochemical detection procedures, such as those disclosed in published International Patent Application No. PCT/US98/12082 entitled "Detection of Analytes Using Reorganization Energy," published International Patent Application No. PCT/US98/12430 entitled "Electronic Methods for the Detection of Analytes," and in published International Patent Application No. PCT/US97/20014 entitled "Electrodes Linked Via Conductive Oligomers to Nucleic Acids" the oligonucleotide probe is not required to harbor a detectable label.

Acceptability of the final product following synthesis and purification of an oligonucleotide may be verified by any of several procedures. First, polyacrylamide gel electrophoresis can be used to determine the size and purity of the oligonucleotide according to standard laboratory methods (see *Molecular Cloning: A Laboratory Manual*, Sambrook et al., eds. Cold Spring Harbor Lab Publ., 11.51, (1989)).

Alternatively, High Pressure Liquid Chromatography ("HPLC") procedures can be used for this same purpose.

Hybridization between the labeled oligonucleotide probe and target nucleic acid in the procedures described below can be enhanced through the use of unlabeled "helper oligonucleotides" according to the procedure disclosed by Hogan et al., in U.S. Pat. No. 5,030,557 entitled, "Means and Methods for Enhancing Nucleic Acid Hybridization." As indicated above, helper oligonucleotides bind a region of the target nucleic acid other than the region that is bound by the assay probe. This binding imposes new secondary and tertiary structures on the targeted region of the single-stranded nucleic acid and accelerates the rate of probe binding. Helper oligonucleotides which can be used in combination with labeled oligonucleotide probes of the present invention are preferably up to 100 nucleotides in length and have a sequence that includes at least 26 contiguous nucleotides, more preferably at least 35 contiguous nucleotides, still more preferably at least 41contiguous nucleotides, even more preferably at least 43 contiguous nucleotides contained within the sequence of SEQ ID NO:7.

Those having ordinary skill in the art will appreciate that factors affecting the thermal stability of a probe:target hybrid also can influence probe specificity. Accordingly, the melting profile, including the melting temperature (Tm) of probe:target hybrids, should be empirically determined for each probe:target combination. A preferred method for making this determination is described by Arnold et al., in U.S. Pat. No. 5,283,174, entitled "Homogeneous Protection Assay."

One approach for measuring the Tm of a probe:target hybrid involves conducting a hybridization protection assay. According to the method of this assay, a probe:target hybrid is formed under conditions of target excess in a lithium succinate buffered solution containing lithium lauryl sulfate. Aliquots of the "preformed" hybrids are diluted in the hybridization buffer and incubated for five minutes at various temperatures starting below the anticipated Tm (typically 55° C.) and increasing in 2–5 degree increments. This solution is then diluted with a mildly alkaline borate buffer and incubated at a lower temperature (for example 50° C.) for ten minutes. An acridinium ester (AE) linked to a single-stranded probe will be hydrolyzed under these conditions while an acridinium ester linked to a hybridized probe will be relatively "protected." This procedure is referred to as the hybridization protection assay ("HPA"). The amount of chemiluminescence remaining is proportional to the amount of hybrid and is measured in a luminometer by addition of hydrogen peroxide followed by alkali. The data is plotted as percent of maximum signal (usually from the lowest temperature) versus temperature. The Tm is defined as the point at which 50% of the maximum signal remains.

In an alternative approach, the Tm of a probe:target hybrid can be determined using an isotopically labeled probe. In all cases, the Tm for a given hybrid will vary depending on the concentration of salts, detergents and other solutes contained in the hybridization solution. All of these factors influence relative hybrid stability during thermal denaturation (*Molecular Cloning: A Laboratory Manual* Sambrook et al., eds. Cold Spring Harbor Lab Publ., 9.51 (1989)).

The rate at which a probe hybridizes to its target is a measure of the thermal stability of the target secondary structure in the probe region, and can be determined using $C_0t_{1/2}$ measurements. These kinetic measurements of hybridization rate have units of (moles of nucleotide per liter)×(seconds). Expressed more simply, the $C_0t_{1/2}$ value is the concentration of probe times the half-life of hybridization at that concentration. This value can be determined by hybridizing various amounts of probe to a constant amount of target nucleic acid for a fixed time. For example, 0.05 pmol of target is incubated with 0.012, 0.025, 0.05, 0.1 and 0.2 pmol of probe for 30 minutes. The $C_0t_{1/2}$ may also be determined by hybridizing the target and probe under conditions of target excess and then measuring the increase of duplex formation over time. The amount of hybrid present can be measured using the above-described HPA procedure or by scintillation counting if a radiolabeled probed is used in the procedure. The measured signal, when using AE labeled probe, is then plotted as the log of the percent of maximum Relative Light Units ("RLU") from the highest probe concentration versus probe concentration (moles of nucleotide per liter). The $C_0t_{1/2}$ is graphically determined from the concentration corresponding to 50% of maximum hybridization multiplied by the hybridization time in seconds. These values range from $9\times10^{-6}$ to $9\times10^{-5}$ with the preferred values being less than $3.5\times10^{-5}$. Similar values may be obtained by measuring radioactivity and plotting % hybridization at a given time point vs maximum extent.

In a preferred method of determining whether a biological sample contains rRNA or rDNA that would indicate the presence of any one of *Candida albicans, Candida tropicalis, Candida dubliniensis, Candida viswanathii* and *Candida parapsilosis*, nucleic acids may be released from cells by sonic disruption, for example according to the method disclosed by Murphy et al., in U.S. Pat. No. 5,374, 522. Other known methods for disrupting cells include the use of enzymes, osmotic shock, chemical treatment, and vortexing with glass beads. Other methods suitable for liberating from microorganisms the nucleic acids that can be subjected to the hybridization methods disclosed herein have been described by Clark et al., in U.S. Pat. No. 5,837,452 and by Kacian et al., in U.S. Pat. No. 5,5,364,763. Following or concurrent with the release of rRNA, labeled probe may be added in the presence of accelerating agents and incubated at the optimal hybridization temperature for a period of time necessary to achieve a significant hybridization reaction.

An oligonucleotide having the sequence GCGT-CAATAAAAGAACAACAACCGATCCC (SEQ ID NO:1) was characterized by the criteria of length, Tm and nucleotide sequence and was found to be highly specific for the rRNA of *Candida albicans, Candida tropicalis, Candida dubliniensis, Candida viswanathii* and *Candida parapsilosis*. This polynucleotide, referred to herein as CalA1037, is complementary to a unique segment found in the 18S rRNA of *Candida albicans, Candida tropicalis, Candida dubliniensis, Candida viswanathii* and *Candida parapsilosis*. The probe is 29 bases in length, has a Tm of 59.5° C. and hybridized rRNA in a manner that was enhanced by the presence of helper oligonucleotides.

This probe is one illustration of an oligonucleotide that: (1) hybridizes the target nucleic acid under high stringency hybridization conditions, (2) has a length of up to 100 nucleotide bases, and (3) includes at least 15 contiguous nucleotides falling within the sequence identified by SEQ ID NO:7 or its complement. Other oligonucleotides having these properties are contemplated for use as hybridization assay detection probes and are embraced by the invention.

Similarly, oligonucleotides having the sequences of SEQ ID NOs:2, 3 and 4 are disclosed herein as illustrations of useful helper oligonucleotides that are highly preferred for conducting hybridization procedures.

A probe oligonucleotide identified by SEQ ID NO:5 (called CalA1038) and a helper oligonucleotide identified by SEQ ID NO:6 (called CalA1005) also were tested and shown to be useful for hybridizing the rRNA of Candida species. Like the probe and helper oligonucleotides employed in the working Examples herein, these and other probe and helper oligonucleotides embraced by the invention also have sequences of up to 100 nucleotides in length, or up to 60 nucleotides in length, and further have at least 15, more preferably at least 26, still more preferably at least 28, and yet still more preferably at least 29 contiguous nucleotides contained within the sequence identified by SEQ ID NO:7 or its complement.

As indicated below, the highly preferred CalA1037 probe specifically hybridized Candida albicans, Candida tropicalis, Candida dubliniensis, Candida viswanathii and Candida parapsilosis rRNAs in a manner that was promoted by the use of helper oligonucleotides. According to the procedure used to make this determination, single-stranded probe oligonucleotide radiolabeled at the 5'-end was contacted with rRNA from Candida albicans in the presence or absence of helper oligonucleotides. Probe molecules hybridizing the rRNA to form double-stranded hybrids were separated from single-stranded probe molecules by hydroxyapatite capture. The double-stranded hybrids bound to the hydroxyapatite and were detected and quantitated by scintillation counting. As indicated below, the Tm of the probe:target hybrid advantageously was significantly increased in the presence of one or more helper oligonucleotides.

The following Example describes the methods used to demonstrate that the CalA1037 probe hybridized rRNA from Candida albicans and that this interaction was facilitated by including helper oligonucleotides in the hybridization mixture.

EXAMPLE 1

Tm Determination for Probe:Target Hybrids

Tm values for probe:target and helper:target hybrids were determined using an end-labeled CalA1037 probe having the sequence of SEQ ID NO:1 and end-labeled helper oligonucleotides selected from the group: (A) OMeTCalA1013, (B) CalA996 and (C) CalA1066. The sequence of the CalA1037 probe is given above. The sequence of OMeTCalA1013 is TAGTCGGCATAGTTTATGGTTAAGAC (SEQ ID NO:2), the sequence of CalA996 is TAGTCGGCATAGTTTATGGTTAAGACTACGACGGTATCTGATC (SEQ ID NO:3) and the sequence of CalA1066 is CCCAGAACCCAAAGACTTTGATTTCTCGTAAGGTGCCGATT (SEQ ID NO:4). Helper oligonucleotides A, B and C were selected to bind target rRNA molecules immediately adjacent to the probe. The probe and helper oligonucleotides were 5'-end labeled using [$\gamma$-$^{32}$P]ATP as a phosphate donor and T4 polynucleotide kinase to catalyze the phosphate transfer reaction essentially as described in Molecular Cloning: A Laboratory Manual (Sambrook et al., eds. Cold Spring Harbor Lab Publ. 10.59 (1989)). End-labeled helper and probe oligonucleotides were separately combined with purified rRNA from Candida albicans to provide conditions of target excess. In trials that included both the probe and helper oligonucleotides, only the probe was end-labeled and each helper oligonucleotide was present in at least a 10 fold molar excess over the Candida albicans rRNA that served as a target. All mixtures were hybridized to completion in a solution that included 0.48 M sodium phosphate buffer, 0.1% sodium dodecyl sulfate, 1 mM EDTA and 1 mM EGTA. As negative controls, the probe and/or helper oligonucleotides were hybridized in the absence of the nucleic acid target. At the conclusion of the hybridization procedure, mixtures were diluted and passed over a hydroxyapatite column to separate single-stranded nucleic acids from double-stranded hybrids. The amount of radioactivity in the column flow-through represented single-stranded probe and was measured by scintillation counting. The amount of radioactivity bound to the hydroxyapatite was separately measured by scintillation counting. Results of these procedures are presented in Table 1.

TABLE 1

Hybridization of Probe and/or Helper Oligonucleotides with Target rRNA

| Oligonucleotide | Tm (° C.) |
|---|---|
| CalA1037 (Probe) | 59.5 |
| OMeTCalA1013 (Helper) | 81.3 |
| CalA996 (Helper) | 68.0 |
| CalA1066 (Helper) | 75.0 |
| Probe + CalA996 | 61.7 |
| Probe + OMeTCalA1013 | 61.0 |
| Probe + CalA1066 | 61.0 |
| Probe + CalA996 + CalA1066 | 63.2 |
| Probe + OMeTCalA1013 + CalA1066 | 64.0 |

The results from this procedure confirmed that the end-labeled probe hybridized rRNA from Candida albicans and indicated that the Tm of the interaction advantageously increased when helper oligonucleotides were included with the probe in the hybridization reaction. We particularly observed that the Tm of the probe:target complex could be increased from 59.5 to 64.0° C. when the combination of OMeTCalA1013 and CalA1066 helper oligonucleotides were included in the hybridization reaction. While not shown in Table 1, our results indicated that the extent of probe hybridization was increased by the presence of helper oligonucleotides in the hybridization reaction. Although the probe can be used either alone or in combination with one or more helper oligonucleotides in hybridization procedures, the below-described experiments to characterize the probe were conducted using the probe in combination with the OMeTCalA1013 and CalA1066 helper oligonucleotides. Combinations of probe and helper oligonucleotides useful in the procedures described herein preferably have probe:target Tm values in the range of from about 60–65° C. under the conditions described above.

Probe specificity was confirmed by demonstrating positive hybridization to rRNAs from a specificity panel. The collection of organisms used as sources of target nucleic acids in this procedure represented a taxonomic cross-section of organisms and a nearest-neighbor group. In the following procedure, quantitative results using the AE-labeled hybridization probe were compared to the amount of fungal rRNA present in each sample using a positive control probe. This positive control probe, which hybridized rRNA from all species of fungi, was particularly useful for confirming the presence of fungal rRNA in samples that failed to hybridize the CalA1037 probe.

The following Example describes the methods used to demonstrate that the CalA1037 probe specifically hybridized rRNAs from only a subset of Candida species.

EXAMPLE 2

Verification of Probe Specificity

Fungal lysates or purified RNA were used as nucleic acid targets for hybridization of a CalA1037 probe having the sequence of SEQ ID NO:1, together with helper oligonucleotides having the sequences of OMeTCalA1013 (SEQ ID NO:2) and CalA1066 (SEQ ID NO:4). Organisms employed as sources of rRNA in this procedure were either typed clinical isolates or obtained from the American Type Culture Collection (ATCC). All samples are identified in Table 2 by master log numbers for Gen-Probe Incorporated. Parallel samples of each rRNA were hybridized with a labeled pan-fungal positive control probe having the sequence GTCTGGACCTGGTGAGTTTCCC (SEQ ID NO:9) and unlabeled methoxy helper oligonucleotides having the sequences CGTGTTGAGTCAAATTAAGCCGC (SEQ ID NO:10) and GCTCTCAATCTGTCAATCCTTATTGT (SEQ ID NO:11). The hybridization solution contained 0.6M LiCl, 1% lithium lauryl sulfate, 60 mM lithium succinate and 10 mM each of EDTA and EGTA, pH 5.5. Both the CalA1037 probe and the positive control probe were labeled with acridinium ester essentially according to the method disclosed in U.S. Pat. No. 5,185,439, entitled "Acridinium Ester Labeling and Purification of Nucleotide Probes." At the conclusion of the hybridization reaction, acridinium ester linked to unhybridized probe was rendered non-chemiluminescent under mild alkaline conditions, while acridinium ester attached to hybridized probe remained resistant to the inactivation. Conditions for the hydrolysis and detection of hybridized probe labeled with acridinium ester are described by Arnold et al., in Clin. Chem. 35:1588 (1989)). The magnitudes of probe hybridization in these procedures were quantitated by luminometry using procedures familiar to those having ordinary skill in the art. The magnitude of the CalA1037 probe signal was then divided by the magnitude of the fungal positive control signal to normalize results in the study. Samples having CalA1037 probe signals that were greater than about 10% of the positive control signal indicated specific hybridization with the CalA1037 probe, while lower values indicated negative results. Assay results are shown in Table 2.

TABLE 2

Hybridization of the CalA1037 Probe and rRNA-Containing Lysates from a Collection of Candida Species

| ORGANISM | *GP# | Pan-Fungal Probe (RLU) | CalA1037 Probe (RLU) |
|---|---|---|---|
| Candida albicans | 715 | 165691 | 122584 |
| Candida albicans | 1076 | 157075 | 131178 |
| Candida albicans | 1077 | 165056 | 132884 |
| Candida dubliniensis | 1510 | 188742 | 248966 |
| Candida famata | 1092 | 226822 | 1364 |
| Candida glabrata | 1123 | 168952 | 678 |
| Candida guilliermondii | 1080 | 119251 | 5223 |
| Candida kefyr | 1087 | 586564 | 609 |
| Candida kefyr | 1088 | 397559 | 643 |
| Candida krusei | 716 | 232799 | 599 |
| Candida krusei | 1081 | 200516 | 1147 |
| Candida krusei | 1082 | 179529 | 536 |
| Candida lambica | 1083 | 374086 | 555 |
| Candida lustitaniae | 1084 | 128296 | 1070 |
| Candida parapsilosis | 717 | 152530 | 113440 |
| Candida parapsilosis | 1085 | 198154 | 196603 |
| Candida rugosa | 1089 | 212460 | 1024 |
| Candida tropicalis | 718 | 158167 | 85375 |
| Candida tropicalis | 1091 | 151748 | 188905 |
| Candida tropicalis | 1090 | 154765 | 139727 |
| Candida viswanathii | 1512 | 179243 | 190703 |

*"GP#" entries indicate master log numbers for Gen-Probe Incorporated.

The results presented in Table 2 confirmed that the probe directed against Candida albicans, Candida tropicalis, Candida dubliniensis, Candida viswanathii and Candida parapsilosis rRNA efficiently hybridized rRNA samples from these species.

Specificity of the CalA1037 probe was further investigated by hybridizing labeled probe with a collection of species representing a spectrum of phylogentically diverse organisms. In this procedure, AE-labeled probe was separately mixed with individual rRNA containing lysates from organisms that were outside the Candida genus. Positive hybridization results obtained using the positive control probe and negative results obtained using the CalA1037 probe in the following procedure further indicated that the CalA1037 probe advantageously was highly specific for Candida albicans, Candida tropicalis, Candida dubliniensis, Candida viswanathii and Candida parapsilosis.

The following Example describes additional methods that further demonstrated specificity of the CalA1037 probe. More particularly, the following procedures showed that the CalA1037 probe did not cross hybridize with lysates from non-Candida organisms.

EXAMPLE 3

Absence of Cross Hybridization with Non-Candida Organisms

Hybridization assays were conducted using the AE-labeled probes and helper oligonucleotides according to the procedures described in the previous Example except that lysates containing rRNA isolated from non-Candida species served as target nucleic acids. Results of the procedure are presented in Table 3. A pan-fungal probe having the sequence of SEQ ID NO:9, and helper oligonucleotides having the sequences SEQ ID NO:10 and SEQ ID NO:11 were used as positive controls to detect all fungal rRNAs.

TABLE 3

Hybridization of the CalA1037 Probe with rRNA from a Collection of Non-Candida Organisms

| ORGANISM | GP# | Pan-Fungal Probe (RLU) | CalA1037 Probe (RLU) |
|---|---|---|---|
| Arachniotus flavoluteus | F-932 | 137459 | 616 |
| Aspergillus flavus | F-906 | 145822 | 639 |
| Aspergillus fumigatus | F-899 | 157452 | 638 |
| Aspergillus niger | F-907 | 196897 | 592 |
| Aureobasidium pullulans | F-1108 | 167766 | 1489 |
| Auxarthron thaxteri | F-930 | 164669 | 603 |
| Blastomyces dermatitidis | F1022 | 163500 | 658 |
| Chrysosporuim keratinophilum | F-982 | 174883 | 871 |
| Coccidiodes immitis | F1399 | 165306 | 1031 |
| Cryptococcus albidus var. diffluens | 1020 | 169728 | 743 |
| Cryptococcus neofomans | 1112 | 186216 | 990 |
| Cryptococcus neoformans | 900 | 191183 | 1064 |
| Crytococcus laurentii | 1124 | 151143 | 677 |
| Gymnoascus dugwayensis | F-965 | 221953 | 864 |
| Histoplasma capsulatum | F-968 | 172316 | 762 |
| Microsporum gypseum | F-980 | 192335 | 727 |
| Myxotrichum deflexum | F-933 | 164452 | 738 |

TABLE 3-continued

Hybridization of the CalA1037 Probe with rRNA from a Collection of Non-Candida Organisms

| ORGANISM | GP# | Pan-Fungal Probe (RLU) | CalA1037 Probe (RLU) |
|---|---|---|---|
| *Oidiodendron echinulatum* | F-934 | 160102 | 815 |
| *Penicillium notatum* | F-957 | 162840 | 2222 |
| *Saccharomyces cerevisiae* | 384 | 345986 | 711 |
| *Scopulariopsis acremonium* | F-958 | 138017 | 1702 |
| *Sepedonium chrysospermum* | F-927 | 87447 | 1863 |

*"GP#" entries indicate master log numbers for Gen-Probe Incorporated.

The results presented in Table 3 confirmed that the CalA1037 probe did not cross hybridize with the ribosomal nucleic acids from numerous non-Candida species. Although not specifically presented in Table 3, we repeatedly confirmed that the CalA1037 probe did not substantially hybridize nucleic acids from a human cell line. Taken together with the positive hybridization results presented in the Table 2, it was clear that the CalA1037 probe was highly specific for rRNA of *Candida albicans, Candida tropicalis, Candida dubliniensis, Candida viswanathii* and *Candida parapsilosis*.

In addition to the CalA1037 probe, another probe also was tested and shown to hybridize rRNA of *C. albicans*. This latter probe, called CalA1038, was a single nucleotide shorter at the 3'-end when compared with the CalA1037 probe. To accommodate this difference, an additional helper oligonucleotide, called CalA1005, was created for use in conjunction with the CalA1038 probe.

The following Example describes the methods used to demonstrate that the CalA1038 probe hybridized rRNA from *C. albicans*, and that this interaction could be altered by including helper oligonucleotides in the hybridization mixture.

EXAMPLE 4

Tm Determination for Probe:Target Hybrids

Tm values for the CalA1038 probe, the CalA1005 helper, the CalA1066 helper, and for combinations of the probe and helpers, were determined using a method substantially as described under Example 1. The sequence of the CalA1038 oligonucleotide was GCGTCAATAAAAGAACAACAAC-CGATCC (SEQ ID NO:5). The sequence of the CalA1005 helper oligonucleotide was CTAGTCGGCATAGTTTATG-GTTAAGACTACGACGG (SEQ ID NO:6). The sequence of the CalA1066 helper oligonucleotide is given above. End-labeled helper and probe oligonucleotides were separately combined with rRNA from *C. albicans* to provide conditions of target excess. In trials that included both probe and helper oligonucleotides, only the probe was end-labeled and each helper oligonucleotide was present in at least a 10 fold molar excess over the *C. albicans* rRNA that served as a target. All mixtures were hybridized to completion in a solution that included 0.48 M sodium phosphate buffer, 0.1% sodium dodecyl sulfate, 1 mM EDTA and 1 mM EGTA. At the conclusion of the procedure, mixtures were diluted and passed over a hydroxyapatite column to separate single-stranded nucleic acids from double-stranded hybrids. The amount of radioactivity in the column flow-through represented single-stranded probe and was measured by scintillation counting. The amount of radioactivity bound to the hydroxyapatite was separately measured by scintillation counting. Results of these procedures are presented in Table 4.

TABLE 4

Hybridization of Probe and/or Helper Oligonucleotides with Target rRNA

| Oligonucleotide | Tm (° C.) |
|---|---|
| CalA1038 (Probe) | 57.8 |
| CalA1005 (Helper) | 67.2 |
| CalA1066 (Helper) | 75.0 |
| Probe + CalA1005 | 62.2 |
| Probe + CalA1066 | 59.0 |
| Probe + CalA1005 + CalA1066 | 63.2 |

The results from this procedure confirmed that the end-labeled probe hybridized rRNA from *C. albicans* and indicated that the Tm of the interaction advantageously increased when helper oligonucleotides were included with the probe in the hybridization reaction. It was particularly observed that the Tm of the probe:target complex could be increased from 57.8 to 63.2° C. when the hybridization reaction included both the CalA1005 and CalA1066 helper oligonucleotides. The CalA1038 probe had a Tm lower than that of the CalA1037 probe, and so availability of the CalA1038 probe permits hybridization procedures to be carried out using an alternative hybridization temperature condition.

Like CalA1037, the CalA1038 probe is perfectly complementary over its length to the target sequences found in the 18S rRNAs of *C. albicans, C. tropicalis, C. dubliniensis, C. viswanathii* and *C. parapsilosis*. Thus, demonstration that the CalA1038 probe bound the rRNA target sequence from *C. albicans*, together with knowledge that this rRNA target sequence is present in these other Candida species, compels the conclusion that the CalA1038 probe also would be useful for hybridizing the rRNAs of these other species.

These results confirmed that the novel oligonucleotides disclosed herein were capable of detecting *Candida albicans, Candida tropicalis, Candida dubliniensis, Candida viswanathii* and *Candida parapsilosis*. Moreover, the oligonucleotide probes were capable of distinguishing these Candida species from organisms that were phylogenetically closely related.

This invention has been described with reference to a number of specific examples and embodiments thereof. Of course, a number of different embodiments of the present invention will suggest themselves to those having ordinary skill in the art upon review of the foregoing detailed description. Thus, the true scope of the present invention is to be determined upon reference to the appended claims.

What is claimed is:

1. A compositions for detecting the nucleic acids of a yeast that is any of *C. albicans, C. tropicalis, C. dubliniensis, C. viswanathii* and *C. parapsilosis* said composition comprising an oligonucleotide probe having the length and sequence of SEQ ID NO:1 or the complement thereof or the length and sequence of SEQ ID NO:5 or the complement thereof, and optionally a non-complementary sequence that does not hybridize to the nucleic acids of said yeast.

2. The composition of claim 1, wherein said oligonucleotide probe comprises DNA.

3. The composition of claim 1, wherein the sequence of said oligonucleotide probe consists of SEQ ID NO:1 or SEQ ID NO:5 and does not include said optional non-complementary sequence.

4. The composition of claim 1, wherein said oligonucleotide probe further comprises a detectable label.

5. The composition of claim 3, wherein said oligonucleotide probe further comprises a detectable label.

6. The composition of claim 4, wherein the detectable label is a chemiluminescent label or a radiolabel.

7. The composition of claim 5, wherein the detectable label is a chemiluminescent label or a radiolabel.

8. The composition of claim 7, wherein the detectable label is a chemiluminescent label, and wherein the chemiluminescent label is an acridinium ester.

9. The composition of claim 5, further comprising at least one helper oligonucleotide.

10. The composition of claim 9, wherein said at least one helper oligonucleotide includes at least one nucleotide analog.

11. The composition of claim 10, wherein said at least one nucleotide analog comprises a ribose moiety having a methoxy group disposed at the 2' position.

12. The composition of claim 9, wherein said at least one helper oligonucleotide has the sequence of SEQ ID NO:4.

13. The composition of claim 1, wherein said oligonucleotide probe includes said non-complementary sequence.

14. The composition of claim 13, wherein said non-complementary sequence is selected from the group consisting of a promoter sequence and a restriction endonuclease recognition site.

15. A method of determining whether an organism in the genus Candida is present in a test sample, said method comprising the steps of:

(a) providing to said test sample a composition in accordance with claim 1;

(b) hybridizing under a high stringency condition any nucleic acid that may be present in the test sample with said composition to form a probe:target duplex; and (c) detecting said probe:target duplex, whereby it is determined that an organism that is any of *C. albicans, C. tropicalis, C. dubliniensis, C. viswanathii* and *C. parapsilosis* is present in the sample.

16. The method of claim 15, wherein the sequence of said oligonucleotide probe in step (a) consists of SEQ ID NO:1 or SEQ ID NO:5.

17. The method of claim 16, wherein said test sample may comprise yeast cells, and wherein before step (a) there is a step for releasing nucleic acid from any yeast cells that may be present in said test sample.

18. The method of claim 15, wherein said test sample is a lysate.

19. The method of claim 15, wherein said high stringency condition in step (b) comprises 0.48 M sodium phosphate buffer, 0.1% sodium dodecyl sulfate, 1 mM each of EDTA and EGTA.

20. The method of claim 15, wherein said high stringency condition in step (b) comprises 0.6 M LiCl, 1% lithium lauryl sulfate, 60 mM lithium succinate and 10 mM each of EDTA and EGTA.

21. The composition of claim 16, wherein said oligonucleotide probe in step (a) comprises a detectable label.

22. The method of claim 21, wherein said detectable label is an acridinium ester, and wherein step (c) comprises performing luminometry to detect any of said probe:target duplex.

23. The method of claim 21, wherein said composition in step (a) further comprises at least one helper oligonucleotide.

24. The method of claim 23, wherein said at least one helper oligonucleotide has the sequence of SEQ ID NO:4.

25. A kit for detecting the presence of nucleic acids from any of *C. albicans, C. tropicalis, C. dubliniensis, C. viswanathii and C. parapsilosis* in the sample, said kit comprising:

(a) composition in accordance with claim 1; and (b) at least one helper oligonucleotide.

* * * * *

SEQUENCE LISTING

```
<160> NUMBER OF SEQ ID NOS: 11
<210> SEQ ID NO 1
<211> LENGTH: 29
<212> TYPE: DNA
<213> ORGANISM: Candida albicans

<400> SEQUENCE: 1
gcgtcaataa aagaacaaca accgatccc                                       29

<210> SEQ ID NO 2
<211> LENGTH: 26
<212> TYPE: DNA
<213> ORGANISM: Candida albicans
<220> FEATURE:
<221> NAME/KEY: misc_structure
<222> LOCATION: (1)...(26)
<223> OTHER INFORMATION: Oligonucleotide created using methoxy analogs

<400> SEQUENCE: 2
tagtcggcat agtttatggt taagac                                          26

<210> SEQ ID NO 3
<211> LENGTH: 43
<212> TYPE: DNA
<213> ORGANISM: Candida albicans

<400> SEQUENCE: 3
tagtcggcat agtttatggt taagactacg acggtatctg atc                       43

<210> SEQ ID NO 4
<211> LENGTH: 41
<212> TYPE: DNA
<213> ORGANISM: Candida albicans

<400> SEQUENCE: 4
cccagaaccc aaagactttg atttctcgta aggtgccgat t                         41

<210> SEQ ID NO 5
<211> LENGTH: 28
<212> TYPE: DNA
<213> ORGANISM: Candida albicans

<400> SEQUENCE: 5
gcgtcaataa aagaacaaca accgatcc                                        28

<210> SEQ ID NO 6
<211> LENGTH: 35
<212> TYPE: DNA
<213> ORGANISM: Candida albicans

<400> SEQUENCE: 6
ctagtcggca tagtttatgg ttaagactac gacgg                                35

<210> SEQ ID NO 7
<211> LENGTH: 113
<212> TYPE: DNA
<213> ORGANISM: Candida albicans
<220> FEATURE:
<221> NAME/KEY: misc_structure
<222> LOCATION: (1)...(113)
<223> OTHER INFORMATION: Probe domain

<400> SEQUENCE: 7
```

-continued

```
cccagaaccc aaagactttg atttctcgta aggtgccgat tgcgtcaata aaagaacaac      60
aaccgatccc tagtcggcat agtttatggt taagactacg acggtatctg atc            113
```

<210> SEQ ID NO 8
<211> LENGTH: 113
<212> TYPE: RNA
<213> ORGANISM: Candida albicans
<220> FEATURE:
<221> NAME/KEY: misc_structure
<222> LOCATION: (1)...(113)
<223> OTHER INFORMATION: Sequence of rRNA target region

<400> SEQUENCE: 8

```
gaucagauac cgucguaguc uuaaccauaa acuaugccga cuagggaucg guuguuguuc      60
uuuuauugac gcaaucggca ccuuacgaga aaucaaaguc uuuggguucu ggg             113
```

<210> SEQ ID NO 9
<211> LENGTH: 22
<212> TYPE: DNA
<213> ORGANISM: Candida albicans

<400> SEQUENCE: 9

```
gtctggacct ggtgagtttc cc                                              22
```

<210> SEQ ID NO 10
<211> LENGTH: 23
<212> TYPE: DNA
<213> ORGANISM: Candida albicans

<400> SEQUENCE: 10

```
cgtgttgagt caaattaagc cgc                                             23
```

<210> SEQ ID NO 11
<211> LENGTH: 26
<212> TYPE: DNA
<213> ORGANISM: Candida albicans

<400> SEQUENCE: 11

```
gctctcaatc tgtcaatcct tattgt                                          26
```